United States Patent
Davis et al.

(10) Patent No.: US 10,578,567 B2
(45) Date of Patent: Mar. 3, 2020

(54) METHODS FOR QUANTIFYING RUBBER CONTENT IN A PLANT WITH NMR

(71) Applicant: Bridgestone Corporation, Chuo-ku (JP)

(72) Inventors: Michael C. Davis, Independence, OH (US); Yingyi Huang, Hudson, OH (US)

(73) Assignee: Bridgestone Corporation, Chuo-ku (JP)

( * ) Notice: Subject to any disclaimer, the term of this patent is extended or adjusted under 35 U.S.C. 154(b) by 75 days.

(21) Appl. No.: 15/540,767

(22) PCT Filed: Dec. 29, 2015

(86) PCT No.: PCT/US2015/067890
§ 371 (c)(1),
(2) Date: Jun. 29, 2017

(87) PCT Pub. No.: WO2016/109554
PCT Pub. Date: Jul. 7, 2016

(65) Prior Publication Data
US 2018/0052122 A1 Feb. 22, 2018

Related U.S. Application Data

(60) Provisional application No. 62/097,227, filed on Dec. 29, 2014.

(51) Int. Cl.
*G01N 24/08* (2006.01)
*G01R 33/44* (2006.01)
(Continued)

(52) U.S. Cl.
CPC ......... *G01N 24/08* (2013.01); *G01N 33/0098* (2013.01); *G01R 33/445* (2013.01); *G01R 33/448* (2013.01); *G01R 33/465* (2013.01)

(58) Field of Classification Search
None
See application file for complete search history.

(56) References Cited

U.S. PATENT DOCUMENTS

| 5,675,253 A | 10/1997 | Smith et al. |
| 6,072,576 A | 6/2000 | McDonald et al. |
| (Continued) | | |

FOREIGN PATENT DOCUMENTS

WO 9714063 A1 4/1997

OTHER PUBLICATIONS

Tonnet et al., "Estimation of Rubber Content of Guayule Using Low-Resolution Proton Magnetic Resonance" 1983, J.Sci.Food Agric. (Year: 1983).*

(Continued)

*Primary Examiner* — Douglas X Rodriguez
(74) *Attorney, Agent, or Firm* — Meredith E. Hooker; J. Gregory Chrisman

(57) ABSTRACT

Methods are described for quantifying an amount of natural rubber in a plant from a sample of the plant by obtaining a $T_1$ spin-lattice relaxation rate or $T_2$ spin-spin relaxation rate from a NMR apparatus, such as a low-field NMR apparatus operating at a magnetic field strength of 2 T or less. The NMR relaxation rates obtained from the plant sample are compared to reference relaxation data or plots. The plots can represent the weight percent polyisoprene versus $T_1$ spin-lattice relaxation rate or $T_2$ spin-spin relaxation rate. The reference relaxation data or plots are generated from testing the same type of plant as the sample.

13 Claims, 10 Drawing Sheets

(51) Int. Cl.
   *G01R 33/465* (2006.01)
   *G01N 33/00* (2006.01)

(56) References Cited

U.S. PATENT DOCUMENTS

| | | | |
|---|---|---|---|
| 6,437,565 B1 | 8/2002 | Early et al. | |
| 2013/0302851 A1 | 11/2013 | Fraley | |
| 2014/0212901 A1* | 7/2014 | Lowery, Jr. | G01N 24/08 435/13 |

OTHER PUBLICATIONS

"Quantitative analysis of isoprene units in natural rubber and synthetic polyisoprene using H-NMR spectroscopy with an internal standard" 2015, Polymer Testing (Year: 2015).*

Ghambir, P.N. Quick Determination of Dry Rubber Content in Natural Rubber Latex by Low-resolution Pulsed NMR Technique, 1993, Journal of Natural Rubber Research, vol. 8, Issue 3, p. 208-212 (Year: 1993).*

Tonnet, et al.; Estimation of Rubber Content of Guayule (Parthenium argentatum) Using Low-Resolution Proton Magnetic Resonance; J. Sci. Food Agric, 1983, 34, 16-174.

VisIntainer, et al.; Determination of Rubber Content in Guayule Bushes by Carbon-13 Nuclear Magnetic Resonance Spectrometry; Anal. Chem. 1981, 53, 1570-1572.

Nurthen, et al; Modified Soxhlet Procedure for the Quantification of Resin and Rubber Content of Guayule; Anal. Chem., 58, 448-453.

Spence, et al.; Determination of Rubber in Rubber-Bearing Plants; Rubber Chemistry and Technology, Mar. 1934, 7, 1, 111-124.

I. S. Choi and C. M. Roland (1997) Strain-Crystallization of Guayule and Hevea Rubbers. Rubber Chemistry and Technology: May 1997, vol. 70, No. 2, pp. 202-210.

Fukumori, et al.; Swelling behaviour of rubber vulcanizates: Real-Time pulsed nuclear magnetic resonance measurements; Polymer, Apr. 1990; 31, 4, 713-720.

Extended European Search Report issued in corresponding European Patent Application No. 15876180.9; dated Sep. 17, 2018.

Supplementary European Search Report issued in corresponding European Patent Application No. 15876180.9; dated Oct. 5, 2018.

* cited by examiner

| SAMPLE | WEIGHT % RUBBER | WIDTH | A(1) | T2(1) | A(2) | T2(2) | A(1) | T1 |
|---|---|---|---|---|---|---|---|---|
| 1 | 2.5 | 0.208 | 81.3 ± 0.7 | 1.67 ± 0.04 | 18.6 ± 0.4 | 18.7 ± 0.6 | -131 ± 2 | 72 ± 4 |
| 2 | 5 | 0.222 | 85.8 ± 0.5 | 1.5 ± 0.03 | 14.2 ± 0.5 | 13.8 ± 0.5 | -161 ± 2 | 62 ± 2 |
| 3 | 7 | 0.249 | 87.1 ± 0.6 | 1.5 ± 0.03 | 12.9 ± 0.4 | 13.2 ± 0.5 | -184 ± 1 | 39.4 ± 0.7 |
| 4 | 11 | 0.271 | 92.4 ± 0.5 | 1.28 ± 0.03 | 7.6 ± 0.4 | 11.5 ± 0.7 | -236 ± 4 | 28 ± 1 |

METHODS FOR QUANTIFYING RUBBER CONTENT IN A PLANT WITH NMR

TECHNICAL FIELD

The present invention relates to a method for quantifying an amount of natural rubber in a plant from testing a plant sample, and more particularly, comparing and using NMR data and relaxation rates obtained from an NMR apparatus used to test the plant sample to reference data, relaxation rates and calibration curves or charts generated from testing samples from the same type of plant.

BACKGROUND

Certain plants represent sustainable sources of natural rubber. Natural rubber can be extracted from such plants for use industry, for example, in the tire, medical and consumer products industries. One plant, guayule, is a perennial shrub that is a renewable source of natural rubber. The natural rubber extracted from guayule, which is native to Southwestern U.S., can replace petroleum-based synthetics and reduce reliance on imported natural rubber. The guayule is desirable because it advantageously requires relatively low amounts of water and pesticides, which reduces the costs of raising and harvesting this sustainable source of natural rubber. Another plant, the hevea tree, is also a renewable source of natural rubber. The hevea tree represents the primary source of natural rubber used in tire production.

Breeding and harvesting methods for rubber-bearing plants focus on maximizing the amount of available extractable rubber. Rapid screening methods for estimating the amount of natural rubber in harvestable plants has proven difficult. For example, guayule, which has rubber throughout its plant tissues, often requires time intensive methods, such as solvent extraction and lengthy sample preparation, for estimating extractable rubber content. Sample preparation, extraction methods and long analysis times can substantially limit the number of analyses which can be completed each day. Further, methods based on the use of high resolution or high-field NMR spectrums require expensive and large equipment having strong magnets and cumbersome probe electronics that are not readily transportable to the field. Analysis time using high resolution NMR apparatuses is lengthy and thus such use is not suitable for rapid screening of plants, either in the lab or field. There remains a need for more robust and accurate methods for quantifying natural rubber in a plant, and further for rapid, field-ready methods for accurately quantifying the amount of natural rubber in plants that reduces the costs and lengthy analysis time associated with more sensitive laboratory equipment.

SUMMARY

In a first aspect, provided herein is a method for quantifying an amount of natural rubber in a rubber-containing plant by use of NMR. The method includes introducing at least a portion of the plant into a sample receiving space of a NMR apparatus. The NMR relaxation rate is generated by performing NMR relaxometry on the portion of the plant with the NMR apparatus, and the NMR relaxation rate is the $T_1$ spin-lattice relaxation rate of the portion of the plant over time or the $T_2$ spin-spin relaxation rate of the portion of the plant over time. The amount of natural rubber in the plant is quantified by comparing the NMR relaxation rate or processed rate information obtained from the portion of the plant to reference data generated from testing the same type of plant as the portion of the plant.

In an example of aspect 1, the plant is a guayule plant and the amount of quantified natural rubber is the amount of extractable natural rubber contained the tested guayule plant.

In another example of aspect 1, the method is non-destructive to the plant wherein the portion of the plant used in the sample receiving space of the NMR apparatus to quantify an amount of natural rubber in the plant is less than 5 weight percent of the plant.

In another example of aspect 1, the NMR apparatus operates at a magnetic field strength of 2 T or less for obtaining the NMR relaxation rate for the portion of the plant.

In another example of aspect 1, the method is performed on the portion of the plant in less than 10 minutes, or less than 5 minutes, and the NMR apparatus is a low-field NMR apparatus.

In another example of aspect 1, the reference data is a reference relaxation plot of $T_2$ spin-spin relaxation rate versus weight percent polyisoprene for the type of plant as tested and the step of quantifying an amount of natural rubber in the plant includes comparing the $T_2$ spin-spin relaxation rate of the portion of the plant to the reference relaxation plot.

In another example of aspect 1, the reference data is a reference relaxation plot of $T_1$ spin-lattice relaxation rate versus weight percent polyisoprene for the type of plant tested and the step of quantifying an amount of natural rubber in the plant includes comparing the $T_1$ spin-lattice relaxation rate of the portion of the plant to the reference relaxation plot.

In another example of aspect 1, the NMR relaxation rate is the $T_2$ spin-spin relaxation rate of the portion of the plant over time and the $T_1$ spin-lattice relaxation rate of the portion of the plant over time, the NMR relaxation rates are compared to a reference relaxation plot of a ratio of $T_1$ spin-lattice to $T_2$ spin-spin relaxation rates versus weight percent polyisoprene to quantify an amount of natural rubber in the plant.

In another example of aspect 1, the method further includes the step of quantifying an amount of resin in the plant by comparing the NMR relaxation rate obtained from the portion of the plant to the reference data, wherein the reference data is a plot of $T_1$ spin-lattice relaxation rate or $T_2$ spin-spin relaxation rate versus weight percent resin.

In another example of aspect 1, the method further includes the step of processing the $T_2$ spin-spin relaxation rate obtained for the portion of the plant using inverse Laplace transformation, and the reference data is a calibration curve generated from the NMR relaxation rate obtained form the portion of the plant processed by using inverse Laplace transformation.

In another example of aspect 1, the processed inverse Laplace transformation of the $T_2$ spin-spin relaxation rate obtained for the portion of the plant is a chart having one or more peaks, at least one peak represents the natural rubber and resin content of the portion of the plant.

In another example of aspect 1, the calibration curve is a plot of the percent area of the peak representing the natural rubber and resin content of the portion of the plant to the total peak area of the chart versus weight percent polyisoprene to quantify an amount of natural rubber in the plant.

In another example of aspect 1, the calibration curve is a plot of the ratio of the area of the peak representing the natural rubber and resin content of the portion of the plant to the total peak area versus weight percent rubber to quantify an amount of natural rubber in the plant.

In another example of aspect 1, the calibration curve is a plot of the intensity of the peak representing the natural rubber and resin content of the portion of the plant versus weight percent rubber to quantify an amount of natural rubber in the plant.

In another example of aspect 1, the portion of the plant tested has at least 1 weight percent resin based on the total weight of the portion of the plant introduced into the receiving space of the NMR apparatus.

The first aspect may be provided alone or in combination with any one or more of the examples of the first aspect discussed above.

In a second aspect, provided herein is a non-destructive method for quantifying an amount of natural rubber in a guayule plant by use of low-field NMR. The method includes introducing a portion of the guayule plant into a sample receiving space of a low-field NMR apparatus, the low-field NMR apparatus operates at a magnetic field strength of 2 T or less for obtaining a NMR relaxation rate for the portion of the guayule plant. The NMR apparatus is used to obtain a $T_2$ spin-spin relaxation rate of the portion of the guayule plant over time. The amount of natural rubber in the guayule plant is quantified by comparing the $T_2$ spin-spin relaxation rate of the portion of the guayule plant to reference data generated from testing the same type of plant as the portion of the tested plant.

In an example of aspect 2, the reference data is a reference relaxation plot of $T_2$ spin-spin relaxation rate versus weight percent polyisoprene.

In another example of aspect 2, the method further includes the step of processing the $T_2$ spin-spin relaxation rate obtained for the portion of the guayule plant using inverse Laplace transformation, and the reference data is a calibration curve generated from the $T_2$ spin-spin relaxation rate obtained form the portion of the guayule plant processed by using inverse Laplace transformation.

In another example of aspect 2, the processed inverse Laplace transformation of the $T_2$ spin-spin relaxation rate obtained for the portion of the guayule plant is a chart having one or more peaks, and at least one peak representing the natural rubber and resin content of the portion of the guayule plant.

In another example of aspect 2, the calibration curve is a plot of the percent area of the peak representing the natural rubber and resin content of the portion of the guayule plant to the total peak area of the chart versus weight percent polyisoprene to quantify an amount of natural rubber in the guayule plant.

The second aspect may be provided alone or in combination with any one or more of the examples of the second aspect discussed above, or with any one or more of the examples of the first aspect.

The accompanying drawings are included to provide a further understanding of principles of the invention, and are incorporated in and constitute a part of this specification. The drawings illustrate one or more embodiment(s), and together with the description serve to explain, by way of example, principles and operation of the invention. It is to be understood that various features disclosed in this specification and in the drawings can be used in any and all combinations. By way of non-limiting example the various features may be combined with one another as set forth in the specification as aspects.

DETAILED DESCRIPTION

Figure 1:
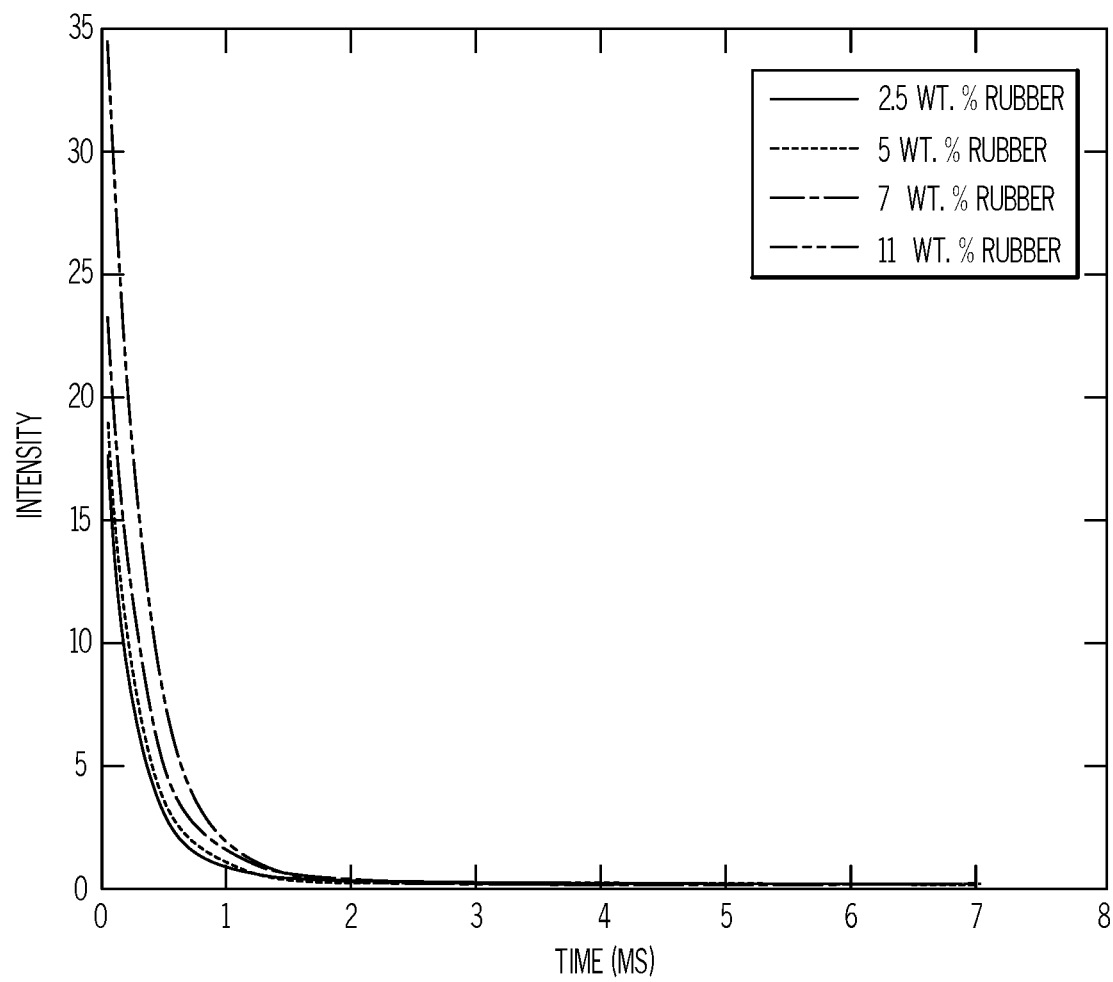
FIG. 1 shows a NMR reference data plot of time domain low-field NMR signal intensity for standardized guayule shrub samples having 2.5, 5, 7 and 11 weight percent polyisoprene.

Herein, when a range such as 5-25 (or 5 to 25) is given, this means preferably at least or more than 5 and, separately and independently, preferably not more than or less than 25. In an example, such a range defines independently at least 5, and separately and independently, not more than 25.

As used herein, "plant" refers to a rubber- or resin-bearing plant and preferably a sustainable rubber producing plant. The term rubber or natural rubber for a plant is also used interchangeably with polyisoprene herein. The plant can be a living, non-harvested plant from which a sample can be taken for testing with an NMR apparatus, for example, a high- or low-field NMR apparatus. In another example, the plant can be a harvested and/or non-living wherein a sample of the plant can be prepared for use with a NMR apparatus. Examples of such plants include, but are not limited to, a guayule shrub (*Parthenium argentatum* Gray) and a hevea tree (*Hevea brasiliensis*). Plant features that can be used for test samples can include any part or combination of parts of the plant, but are not limited to, the stem, leaves, bark, roots or combinations thereof.

The methods described herein can be non-destructive to the plant being tested. Such non-destructive methods are particularly useful to analyze a plant prior to harvesting or for breeding selection. The term "non-destructive" refers to a method for obtaining a sample from a plant for use with a NMR apparatus to quantify an amount of natural rubber or resin in the plant, wherein obtaining the sample does not cause significant harm to the plant or independently cause the plant to die. The non-destructive methods for quantifying an amount of natural rubber or resin in a plant can be used for selective breeding or harvesting purposes that can increase or maximize the amount of extractable rubber that can be obtained from the plants. The methods described herein can also be used to quantify or predict the amount of natural rubber or resin in a non-living or harvested plant. For instance, quantifying the amount of natural rubber in harvested plants, for example samples from multiple harvests, can predict or estimate the total amount of extractable rubber that a particular crop harvest can yield.

The NMR instruments used in the methods and examples described herein can be high- or low-field NMR apparatuses. For example, low-field NMR spectrometers or apparatuses that can record signals from natural rubber (i.e. polyisoprene) and resin present in plant samples. As used herein, the term "low-field" refers to an NMR apparatus that operates at a magnetic field strength of 0.5 to 2 Tesla ("T"), for example, 2 T or less, preferably 1.5 T or less and more preferably 1 T or less. The use of low-field magnets results in less-bulky, transportable NMR apparatuses that are field-ready and that can be used for rapid analysis and screening for quantifying the amount of natural rubber or resin in a plant. A low-field NMR apparatus as described herein may also operate at a resonance frequency in the range of 20 MHz to 90 MHz, for example, 90 MHz or less, preferably 60 MHz or less and more preferably 40 MHz or less. One example of a low-field NMR apparatus is a 0.5 T benchtop Bruker minispec NMR spectrometer that can be used to measure and determine relaxation rate parameters $T_1$ and $T_2$. The low-field NMR apparatus can be equipped with software (e.g., Matlab) for analyzing measured data such as plotting and trending $T_1$ or $T_2$ relaxation data versus weight percent natural rubber. Processing data as described herein can include using inverse Laplace transformation or relaxation rate data and measuring peak characteristics generated from the ILT data for a basis for reference data.

A high-field or high resolution apparatus refers to an NMR apparatus that operates at a magnetic field strength of above 2 T Tesla ("T"), for example, 2.3 to 20 T, 2 T or more, 5 T or more, 10 T or more or 15 T or more. A high-field NMR apparatus as described herein may also operate at a resonance frequency in the range of 100 MHz to 1,000 MHz, for example, 200 MHz or more, 400 MHz or more, 500 MHz or more, 600 MHz or more or 700 MHz or more. One example of a high-field NMR apparatus is a 11.7 T, (500 MHz for $^1$H) Varian Innova NMR spectrometer that can be used to measure and determine relaxation rate parameters $T_1$ and $T_2$. The high-field NMR apparatus can be equipped with software for analyzing measured data such as plotting and trending $T_1$ or $T_2$ relaxation data versus weight percent natural rubber.

As used herein, the term "relaxometry" refers to the study and/or measurement of relaxation parameter variables in nuclear magnetic resonance (NMR). Relaxometry can include, for example, the measurement of a $T_1$ spin-lattice relaxation rate and/or $T_2$ spin-spin relaxation rate with a NMR apparatus and the study and analysis of those measurements to quantify an amount of natural rubber, such as the amount of extractable natural rubber, or resin in a tested plant. The spin-lattice relaxation time, $T_1$, is used to characterize the rate at which equilibrium is established in bulk magnetization. The spin-spin (or transverse) relaxation time constant, $T_2$, is an expression of the relaxation due to non-homogeneities in the local magnetic field over the sensing volume.

Disclosed are methods to quantify the amount of natural rubber or resin in a plant, such as the guayule, using a NMR apparatus (e.g., a low-field NMR apparatus). The methods may also be used to predict the amount of extractable natural rubber in a rubber-containing plant. In one or more embodiments, the amount of extractable natural rubber can be accurately quantified from a plant sample containing natural rubber and resin. That is, the resin does not impact the accuracy of quantifying natural rubber in a plant in a meaningful way. For example, the plant sample can be prepared without extraction or removal of resin present in the sample as harvested or obtained from the plant being tested. The plant sample for testing in the NMR apparatus can contain 0.1 to 15 weight percent resin, 0.5 to 10, 1 to 7.5 or 2, 3, 4, 5 or 6 weight percent resin based on the total weight of the plant material used in the sample. As described below, observing the relaxation rates of a plant sample with a NMR apparatus, in particular a low-field apparatus, allows a user to quickly determine the presence and variant amounts of natural rubber or resin in a the sampled plant.

In the case of time domain NMR or low-field time domain, it was found that measuring a plant sample's $T_1$ spin-lattice relaxation rate and/or $T_2$ spin-spin relaxation rate can be used to accurately quantify the amount of natural rubber is a tested plant. The amount of natural rubber in a plant can be quantified or predicted with the methods described herein at an accuracy of within 0.5 to 5 and preferably 1 to 3 or about 1, 2, or 3 percent of the actual amount of rubber in a tested plant.

In another embodiment, applying an inverse Laplace transform to the $T_2$ spin-spin relaxation rate can be used to generate calibration curves to accurately quantify the amount of natural rubber in a tested plant. The amount of natural rubber in a plant can be quantified or predicted with the methods described herein at an accuracy of within 1 to 15, 2 to 12 or preferably 3 to 10 or about 4, 5, 6, 7 or 8 percent of the actual amount of rubber in a tested plant. The accuracy of using the ILT modified data and calibration curves can be maintained without removing or reducing the amount of resin in the plant sample.

In embodiments, monitoring the NMR signals to quantify an amount of natural rubber or resin in a plant includes obtaining a NMR relaxation rate by performing relaxometry on a portion of a plant by introducing a portion of the plant into a sample receiving space of a NMR apparatus. To test a plant, a portion of the plant must be taken and prepared for use with a NMR apparatus. A plant sample or portion of the plant can include the bark, stem, leaves, root or a combination thereof. As an example, a section of a branch of a plant including stem, bark and leaves can be cut off and prepared to be analyzed in order to quantify the amount of natural rubber in the tested plant. Preparation of the sample can be as known in the art. The size of the plant sample can be adjusted to accommodate the particular NMR apparatus being used, for example, the plant sample can be in the range of 50 mg to 10 g dry weight. For use with conventional NMR tubes, such as a 5 mm or 10 mm sample tube, the plant sample to be analyzed can be in the range of 100 mg to 1 g dry weight. The sample size required to test and quantify the amount of natural rubber in a plant is preferably non-destructive to the plant, such as less than 0.1 to 10 weight percent of the sampled plant.

The portion of the plant to be analyzed with a NMR apparatus can have a water content in the range of 0.1 to 30 weight percent. The plant samples preferably have less than 30, 20, 10, 5, 4, 3, 2 or 1 weight percent of water content prior to testing with a NMR apparatus. To reduce the influence of moisture content on the measured relaxation rates, the plant sample can be dried prior to performing any relaxaometry. For example, samples can be dried in an oven, such as a vacuum oven, at a temperature of 50° to 100° C. for up to 24 hours. The portion of the plant can be chopped and/or milled prior to testing, for example with a chipper, hammer mill or roller mill. The plant sample can have an average piece or particle size in the range of 0.1 to 10 mm. The prepared plant sample can include only plant sample material with no other non-plant materials or ingredients.

The prepared plant sample can be introduced into the sample receiving space of a NMR apparatus to obtain relaxation rates that can be compared to reference relaxation data or further analyzed or adjusted to compare it with calibration curves or data to quantify the amount of rubber or resin in the tested plant. Once the plant sample is prepared and ready for testing, the amount of natural rubber or resin can be quantified with a NMR apparatus (e.g., a low-field NMR apparatus) by the methods described herein within a time period range of 1 to 10 and preferably in 1 to 5 minutes. In one or more embodiments, the methods herein provide a robust and efficient process for testing and screening rubber-bearing plants with short analysis times, for example, not capable with high-field or high resolution NMR apparatuses.

In one embodiment, to quantify an amount of natural rubber in a plant, the obtained NMR relaxation rate from a NMR apparatus can be the $T_2$ spin-spin relaxation rate of the portion of the plant over time. For example, a graph showing the $T_2$ relaxation curve can be generated that plots intensity versus time for the sample, see FIGS. 1, 7, 11, 12 and 13. The obtained $T_2$ spin-spin relaxation rate can be compared to reference relaxation rates generated from testing and standardizing natural rubber content in the same type of plant as the sampled plant. Example 1 below describes a method for generating reference relaxation rates, both $T_1$ and $T_2$, from standardized guayule plant samples of varying weight percent natural rubber. Examples 2 and 3 describe additional methods that can be used to quantify rubber in a plant by processing relaxation rates (e.g., ILT methods) to generate calibration curves. Similar methods can be used to generate reference relaxation rates useful for standardizing natural rubber content in other plants.

Figure 5:
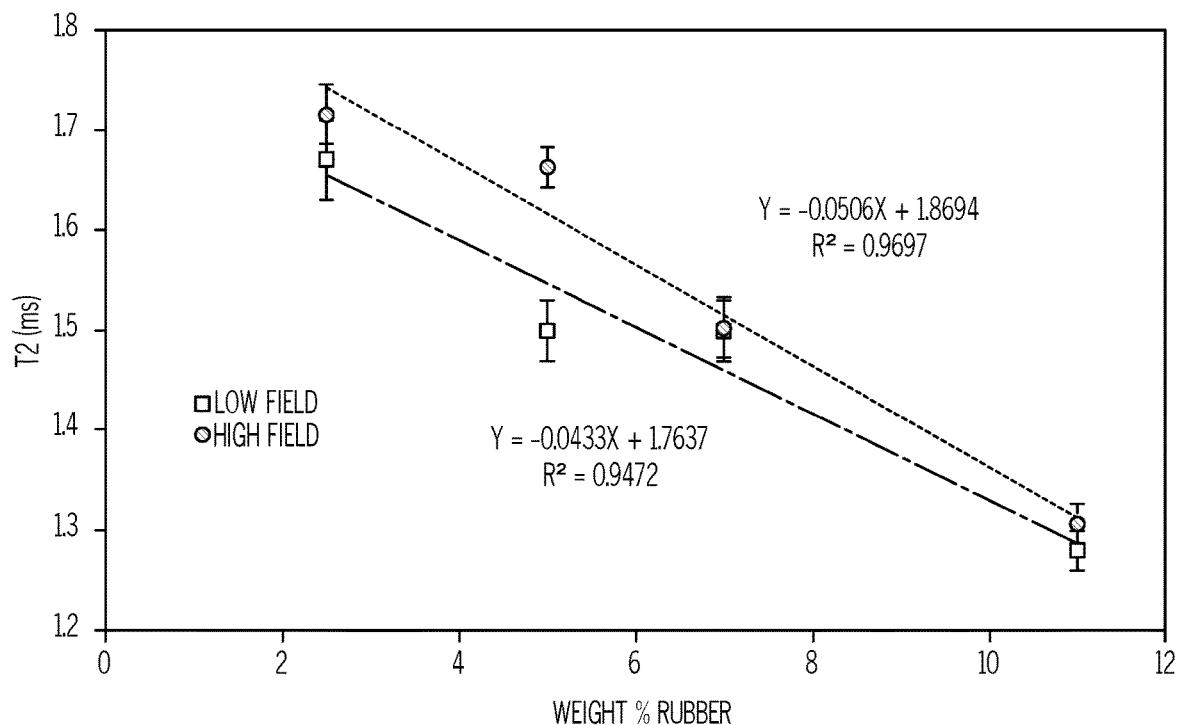
FIG. 5 shows a NMR reference data plot of $T_2$ spin-spin relaxation rates versus weight percent polyisoprene for standardized guayule shrub samples.

The obtained reference relaxation rates from the NMR apparatus can be modified into a reference relaxation plot of $T_2$ spin-spin relaxation rate versus weight percent polyisoprene. Any number of defined rubber concentration samples can be used for generating reference relaxation rates for standardizing the natural rubber content for a particular type of plant. Preferably, two, three, four or more defined rubber concentration samples are used to generate the reference relaxation data. For example, FIG. 5 shows a NMR reference data plot of $T_2$ spin-spin relaxation rates versus weight percent polyisoprene for four standardized guayule shrub samples of known rubber content. Although FIG. 5 is specific to a guayule plant, similar reference relaxation data can be generated to plot reference $T_2$ spin-spin relaxation rates for other rubber-containing plants in order to quantify the amount of natural rubber as described below with regard to FIG. 5.

As shown in FIG. 5, four reference $T_2$ spin-spin relaxation rates are plotted for guayule plant samples containing 2.5, 5, 7 and 11 weight percent polyisoprene. A trend line for the four data points is also shown. The trend line can be used quantify or predict the amount of natural rubber in a guayule plant by comparing the measured $T_2$ spin-spin relaxation rate of a guayule plant sample to the generated trend line characterizing the reference relaxation data. For instance, a user can identify the measured $T_2$ spin-spin relaxation rate on the "y" axis and horizontally connect the measured value with the trend line and, at that intersection, connect that point vertically downward with the "x" axis to determine the weight percent of polyisoprene in the sampled plant.

A trend line, for either $T_1$ or $T_2$ data, as described herein can be customized to encompass the typical range of natural rubber content of the type of plant being tested. As shown, the trend line can be used to quantify the amount of natural rubber in a guayule plant in the range of 2 to 11 weight percent polyisoprene. The trend line can be extrapolated beyond the upper and lower limit of the range to accurately quantify natural rubber in guayule plants having lower or greater amounts of rubber, for example, the trend line can span 1 to 30 weight percent polyisoprene.

A trend line, for either $T_1$ or $T_2$ data, as described herein can also be characterized by an equation that can be used to directly calculate the amount of natural rubber in a sampled plant. For instance, the trend line shown in FIG. 5 is characterized by the equation $y=-0.0433x+1.7637$, wherein the "y" variable is the $T_2$ spin-spin relaxation rate and the "x" variable is the weight percent of polyisoprene. The measured $T_2$ spin-spin relaxation rate of a guayule plant sample can be inserted into the trend line equation to directly calculate the amount of polyisoprene (i.e. the "x" variable) in the guayule plant being tested. The trend line and corresponding trend line equation, and as used in one or more embodiments of the present disclosure, are particularly suited for field use to quantify the amount of natural rubber in a sampled plant after relaxation rate data is obtained from a NMR apparatus.

Figure 6:
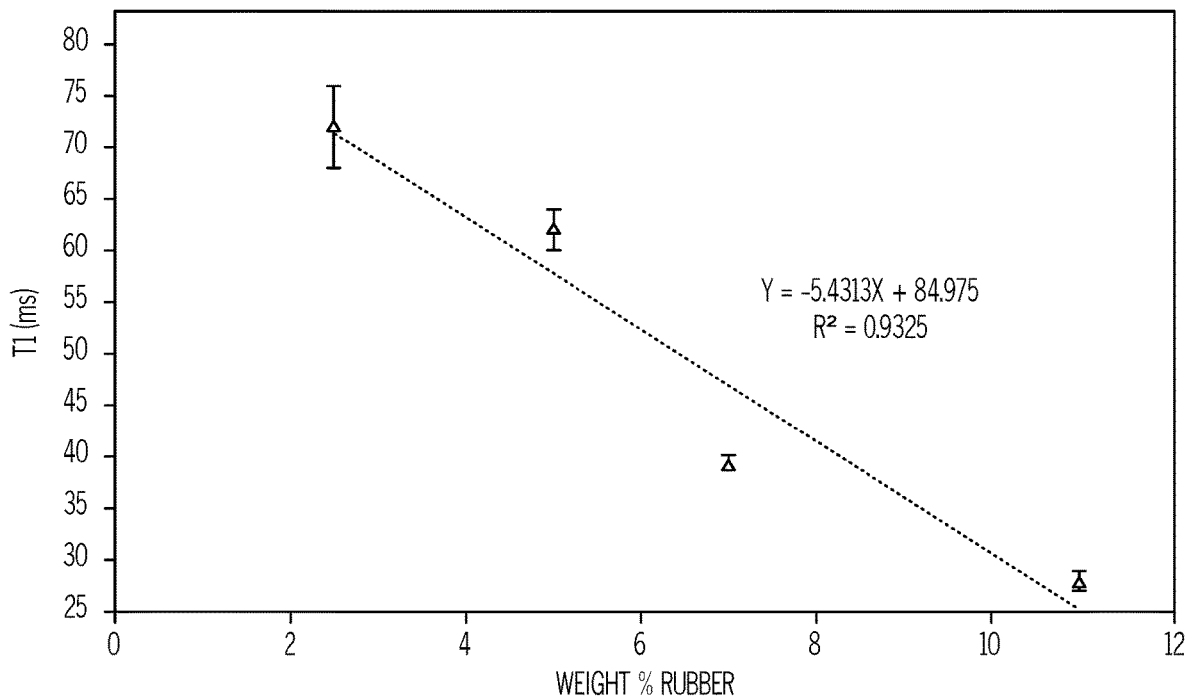
FIG. 6 shows a NMR reference data plot of $T_1$ spin-lattice relaxation rates versus weight percent polyisoprene for standardized guayule shrub samples.

In another embodiment, to quantify an amount of natural rubber in a plant, the obtained NMR relaxation rate from a NMR apparatus can be the $T_1$ spin-lattice relaxation rate of the portion of the plant over time. The $T_1$ spin-lattice relaxation rate can be compared to reference relaxation rates generated from testing the same type of plant as the sampled plant. The reference relaxation rates can be a reference relaxation plot of $T_1$ spin-lattice relaxation rate versus weight percent polyisoprene, for example, as shown in FIG. 6. Similar to the description of FIG. 5 above, although FIG. 6 is specific to the guayule plant, similar data can be measured to generate a plot of reference $T_1$ spin-lattice relaxation rates for other rubber-containing plants in order to quantify the amount of natural rubber.

As shown in FIG. 6, four reference $T_1$ spin-lattice relaxation rates are plotted for guayule plant samples containing 2.5, 5, 7 and 11 weight percent polyisoprene. A trend line for the four data points is also shown. The trend line can be used quantify or predict the amount of natural rubber in a guayule plant by comparing the measured $T_1$ spin-lattice relaxation rate of a guayule plant sample to the generated trend line. As shown, the trend line can be used to quantify the amount of natural rubber in a guayule plant in the range of 2 to 11 weight percent polyisoprene but, as noted above, the trend line can be extrapolated beyond the upper and lower limit of the range to accurately quantify natural rubber in guayule plants having lower or greater amounts of rubber, for example, the trend line can span 1 to 30 weight percent polyisoprene. The trend line can also be customized to include the typical range of natural rubber content of the type of sampled plant.

The trend line shown in FIG. 6 is characterized by the equation y=−5.4313x+84.975, wherein the "y" variable is the $T_1$ spin-lattice relaxation rate and the "x" variable is the weight percent of polyisoprene. The measured $T_1$ spin-lattice relaxation rate of a guayule plant sample can be inserted into the trend line equation to directly calculate the amount of polyisoprene in the guayule plant being tested.

In another embodiment, the reference relaxation data for quantifying the amount of natural rubber in a plant can also include a plot of a ratio of $T_1$ spin-lattice relaxation rate to $T_2$ spin-spin relaxation rate, or vice versa, versus weight percent polyisoprene. The measured $T_1$ spin-lattice relaxation rate and $T_2$ spin-spin relaxation rate for a plant sample can be generated and modified to be shown as a ratio of the two parameters. The adapted $T_1:T_2$ or $T_2:T_1$ ratio can be compared to a reference relaxation plot generated from testing and standardizing natural rubber content in the same type of plant as the sampled plant in order to quantify the amount of natural rubber in a tested plant. The use of two distinct relaxation rates from a sampled plant can minimize error associated with one relaxation parameter and/or provide a more robust characterization of a sampled plant as compared to using only $T_1$ or $T_2$ to quantify the amount of natural rubber in a plant.

In another embodiment, to quantify an amount of resin in a plant, the obtained NMR relaxation rate from a NMR apparatus can be the $T_1$ spin-lattice relaxation rate or the $T_2$ spin-spin relaxation rate of the portion of the plant over time. The measured $T_1$ spin-lattice relaxation rate or $T_2$ spin-spin relaxation rate can be compared to reference relaxation rates generated from testing the same type of plant as the sampled plant. The reference relaxation rates can be modified into a reference relaxation plot of $T_1$ spin-lattice relaxation rate or $T_2$ spin-spin relaxation rate versus weight percent resin. The plot can have a trend line for comparing measured relaxation rates, either $T_1$ or $T_2$, or the measured relaxation rates can be inserted into a trend line equation as described above to directly calculate the amount of resin in a tested plant. The reference relaxation data for quantifying the amount of resin in a plant can also include a plot of a ratio of $T_1$ spin-lattice relaxation rate to $T_2$ spin-spin relaxation rate, or vice versa, versus weight percent resin.

The reference relaxation data, such as $T_1$ and $T_2$ relaxation rates, can be generated by testing the same type of plant as the plant to be quantified by use of NMR, for example low-field NMR. Example 1 described below represents a method for generating reference relaxation data.

In another embodiment, the obtained reference relaxation rates from the NMR apparatus can be in the form of time domain signal intensity and can be further modified by using inverse Laplace transformation. As disclosed herein, any number of defined or known rubber concentration samples can be used for generating reference relaxation rates for standardizing the natural rubber content for a particular type of plant. Using an inverse Laplace transformation of the time domain signal intensity data can generate a plot or chart having multiple peaks that correspond to components of the plant sample or standardized samples that are used to form a calibration curve for use in quantifying or estimating rubber content of plant samples analyzed by NMR.

Figure 8:
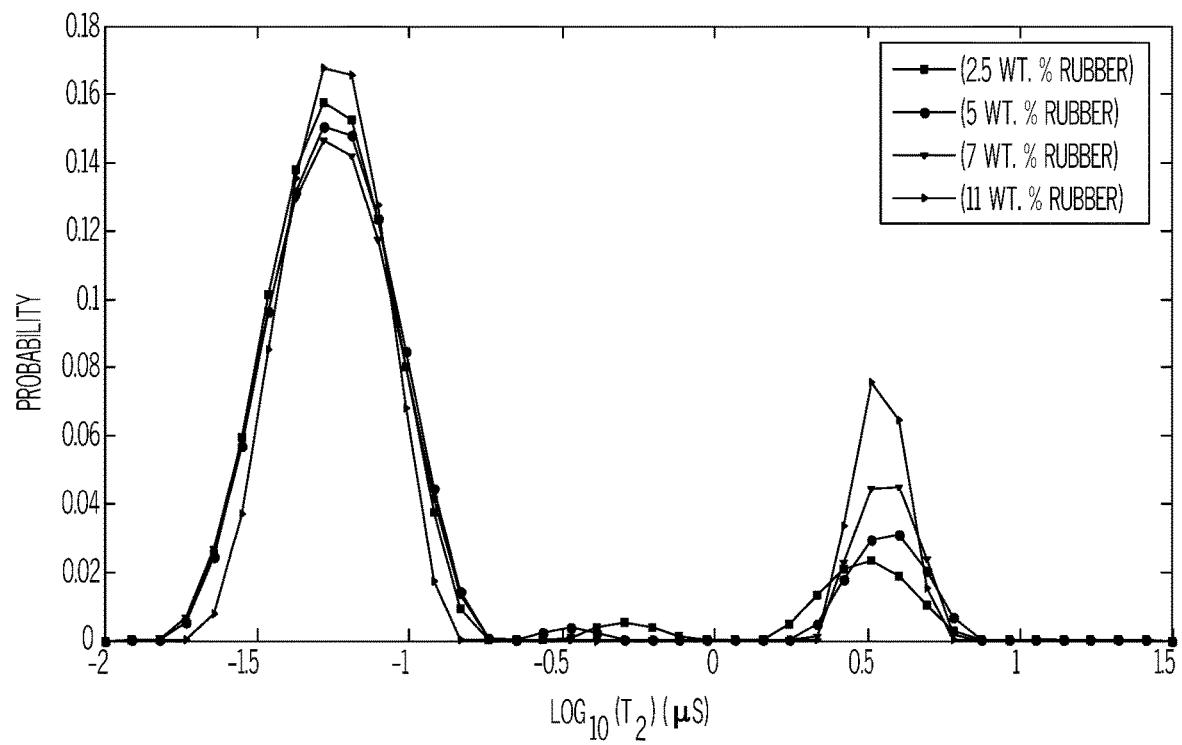
FIG. 8 shows the $T_2$ relaxation data of FIG. 7 processed using inverse Laplace transformation.
Figure 14:
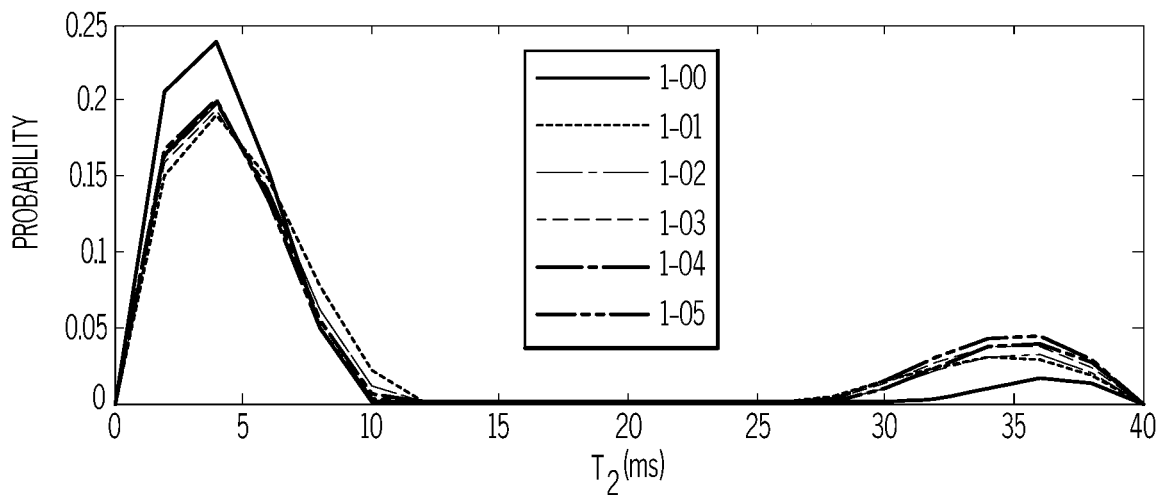
FIG. 14 shows the $T_2$ relaxation data of FIG. 11 processed using inverse Laplace transformation.
Figure 15:
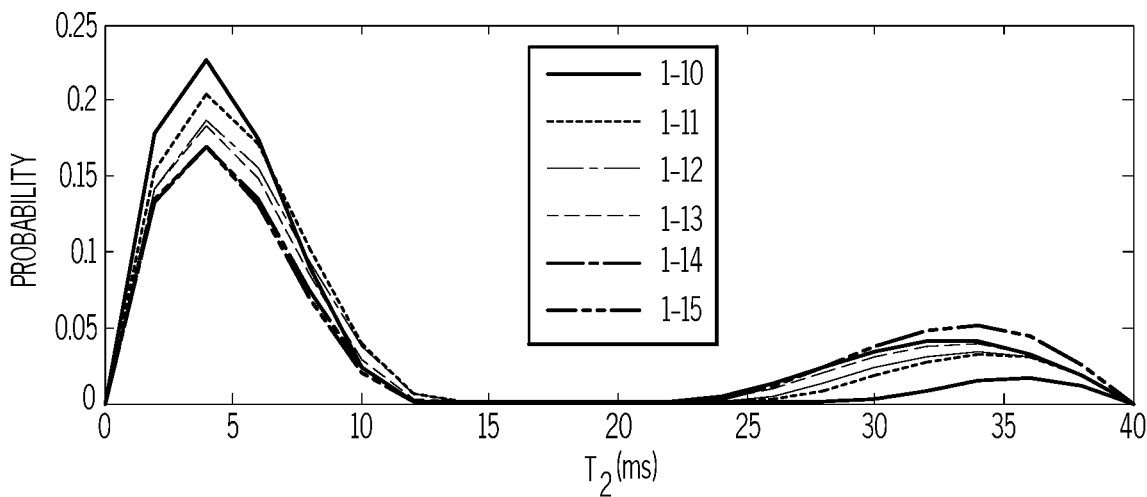
FIG. 15 shows the $T_2$ relaxation data of FIG. 12 processed using inverse Laplace transformation.
Figure 16:
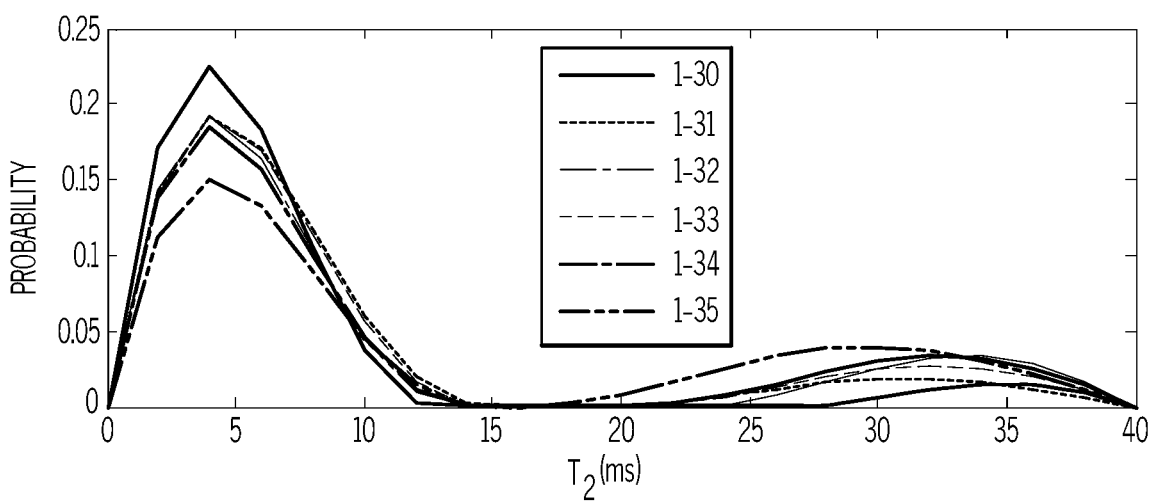
FIG. 16 shows the $T_2$ relaxation data of FIG. 13 processed using inverse Laplace transformation.

For example, the inverse Laplace transform plot can include a peak or peaks corresponding to general plant material and a separate peak corresponding to the rubber component of the sample. In the case resin is present in the sample, the peak corresponding to the rubber component can also include the resin component wherein both components are represented by one peak. For example, FIGS. 8 and 14 shows $T_2$ spin-spin relaxation rate data processed using inverse Laplace transformation. The plot includes multiple sets of at least two distinct peaks for each standardized sample having varying levels of known rubber content. The first primary peak (i.e. having the highest probability value) represents the bulk of the plant material other than the rubber and resin. In an example, FIG. 8 shows the plant material peak as the first and highest peak in the plot, wherein the crest of the peak occurs at about −1.25 μs ($\log_{10}(T_2)$) and the last peak at about a $T_2$ in the range of 0.25 to 0.75 μs ($\log_{10}(T_2)$) is representative of contributions from the rubber and resin. FIGS. 14-16 also show the plant material peak as the first and highest peak in the plot and having a crest at about 4 to 5 ms ($T_2$). The last peak in the figures is representative of the rubber and resin components of the samples.

The inverse Laplace transformation of time domain signal intensity data provides a plot that distinguishes the rubber and resin component of the sample from the remaining plant material. The peak corresponding to the rubber and resin component can be analyzed to determine peak height or intensity, width and area. Similarly, the remaining peaks in the plot (e.g., the plant material peak) can be analyzed to determine peak height, width and area. As shown in FIG. 8, the multiple peaks for each standardized sample having a known concentration of rubber were different as compared to the other various samples with known rubber concentrations. The peak representing the rubber component, and resin if present, can be analyzed to determine the peak area for each plant sample. The peak area can be compared to remaining peak areas or total peak area in the chart to determine a ratio that can be used to plot a reference data for quantifying rubber in other plant samples.

Figure 10:
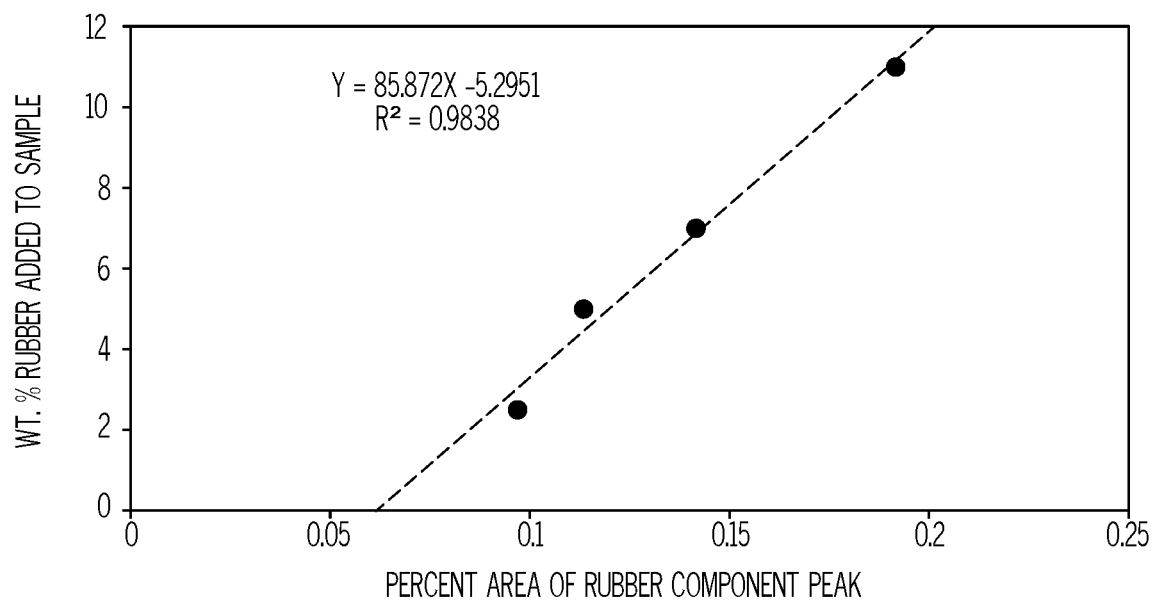
FIG. 10 shows a NMR reference data calibration curve of the percent area of the rubber and resin components peak versus the weight percent of rubber in standardized samples spiked with known amounts of rubber.

The peak area of the rubber component can be compared to the total peak area of the chart (i.e. the sum of the area for each peak present in the chart or plot). The rubber peak area can be further processed to generate a calibration curve that plots the percent area of the rubber component as a portion of the total peak area versus weight percent of rubber in a tested plant sample. In an example, FIG. 10 shows a calibration curve generated from analyzing the inverse Laplace transformation of time domain signal intensity data of standardized plant samples. The calibration curve has four reference data points for each rubber peak corresponding to the standardized plant samples containing 2.5, 5, 7 and 11 weight percent polyisoprene. From the plotted reference data representing the rubber peaks, a trend line can be formed as shown. The trend line can be used quantify or predict the amount of natural rubber in a plant sample (e.g., guayule) by comparing measured $T_2$ spin-spin relaxation rate that has been processed to form the reference trend line of the calibration curve. For instance, a method can include the measured $T_2$ spin-spin relaxation rate of a plant sample is used to determine the intensity signal from the NMR relaxation data, which is further processed using an inverse Laplace transformation to generate a plot having at least a peak corresponding to the rubber component in the sample. The peak area can be measured and compared to the total peak area to determine the percent area of the rubber component peak in the sample. The percent area of the rubber component peak can be used to quantify the amount of rubber in a plant sample by charting peak analysis in relation to the calibration curve.

As shown, the trend line can be used to quantify the amount of natural rubber in a guayule plant in the range of 2 to 11 weight percent polyisoprene but, as noted above, the trend line can be extrapolated beyond the upper and lower limit of the range to accurately quantify natural rubber in guayule plants having lower or greater amounts of rubber, for example, the trend line can span 1 to 30 weight percent polyisoprene. The trend line can also be customized to include the typical range of natural rubber content of the type of sampled plant.

Figure 17:
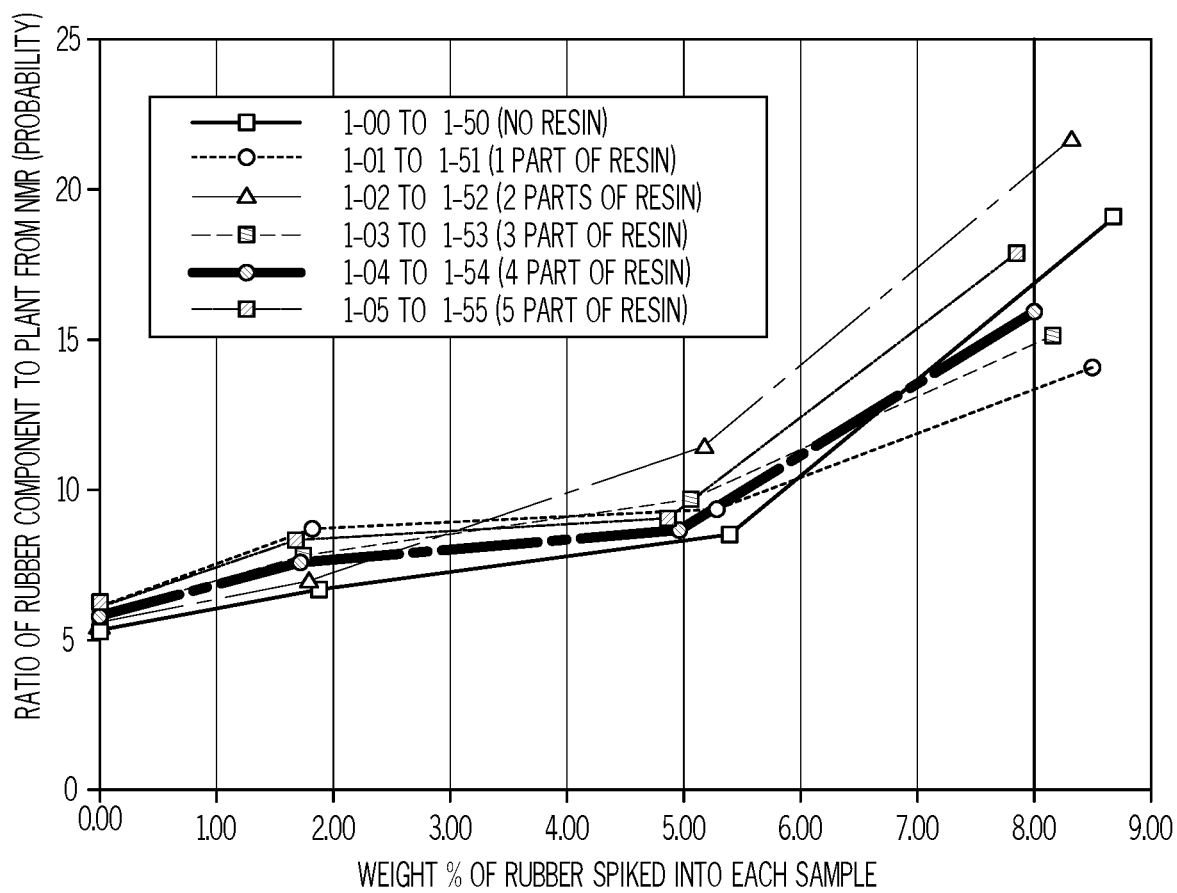
FIG. 17 shows the ratio of the rubber and resin component to the plant material component in the inverse Laplace transformation of NMR relaxation rate data.

In another embodiment, the plot of the inverse Laplace transformation of time domain signal intensity data can be used to calculate the peak areas of the rubber component peak and the plant material peak or peaks. The peak area of the rubber component can be compared to the peak area of the plant material to determine a ratio for multiple standardized samples having known concentrations of rubber and resin. For example, FIG. 17 shows a plot of the ratio of rubber peaks to plant material peaks for multiple standardized plant samples having known quantities of rubber and resin. A calibration curve (e.g. a trend line) can be generated from the reference data as shown in FIG. 17 although a trend line is not shown therein. The trend line can be used quantify or predict the amount of natural rubber in a plant sample (e.g., guayule) by comparing rubber peak area ratio of a tested sample to the trend line. For instance, the measured $T_2$ spin-spin relaxation rate of a plant sample is used to determine the intensity signal from the NMR relaxation data, which is further processed using an inverse Laplace transformation to generate a plot having a peak corresponding to the rubber and other components in the sample. The rubber peak area can be measured and a ratio of rubber peak area to other components can be determined and compared to the reference calibration curve to quantify the amount of rubber in the plant sample.

Figure 18:
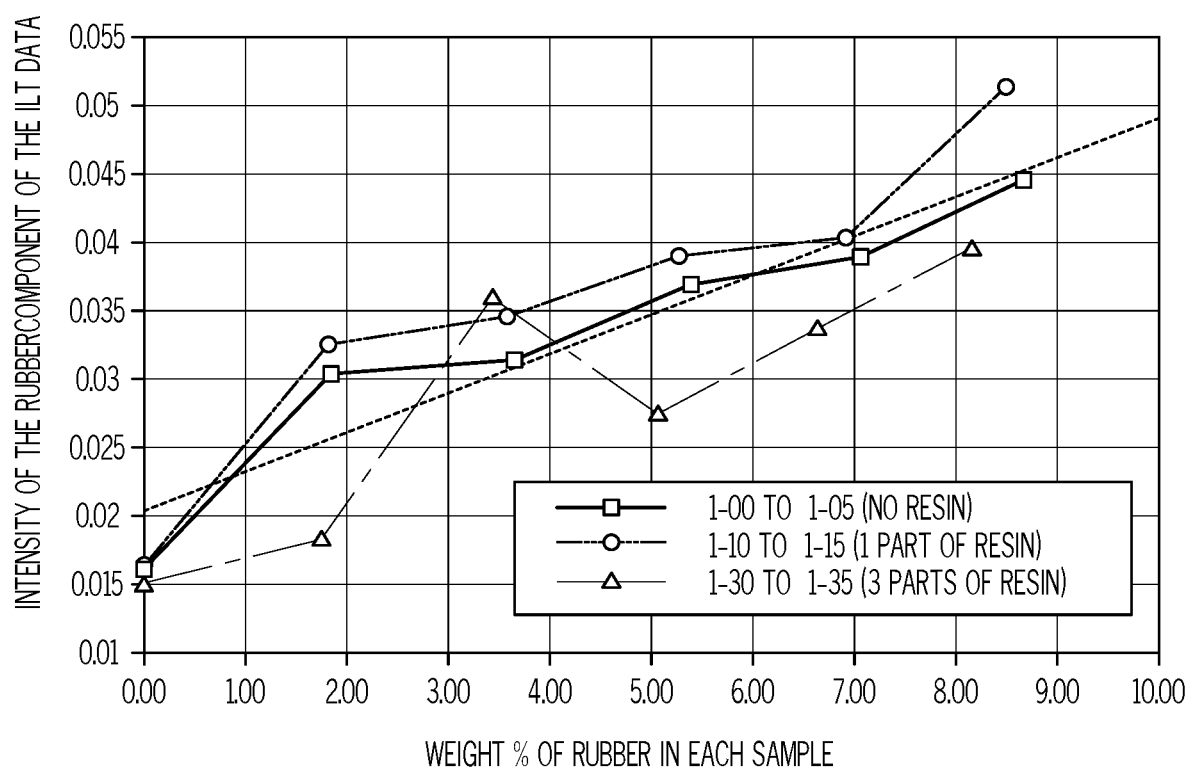
FIG. 18 shows the intensity of the rubber and resin component in the inverse Laplace transformation of NMR relaxation rate data.

In yet another embodiment, the plot of the inverse Laplace transformation of time domain signal intensity data can be used to extract the peak height or intensity of the rubber component peak for each standardized plant sample having a known concentration of rubber and resin. The rubber peak intensity for each standardized sample can be plotted against the weight percent of rubber in the samples to generate a calibration curve for use in estimating rubber content in a plant sample. For example, FIG. 18 shows a calibration curve generated from analyzing the inverse Laplace transformation of time domain signal intensity data. The calibration curve has multiple reference data points for each rubber peak corresponding to the standardized plant samples containing varying amounts of rubber and resin as described in Table 1 of Example 3. From the plotted reference data representing the rubber peak intensities, a trend line can be formed as shown that can function as a calibration curve. The trend line can be used quantify or predict the amount of natural rubber in a plant sample (e.g., guayule) by comparing rubber peak intensity of a tested plant sample to the trend line. For instance, the measured $T_2$ spin-spin relaxation rate of a plant sample is used to determine the intensity signal from the NMR relaxation data, which is further processed using an inverse Laplace transformation to generate a plot having at least a peak corresponding to the rubber component in the sample. The rubber peak height or intensity can be measured and compared to the reference calibration curve, for example as shown in FIG. 18, to quantify the amount of rubber in the plant sample. The quantified rubber content of the plant sample can represent the rubber content for the whole plant that was sampled.

In order to demonstrate the practice of the present disclosure, the following examples have been prepared and tested. The examples should not, however, be viewed as limiting the scope of the invention.

EXAMPLES

Example 1

Generation of Reference Relaxation Data for Guayule Plant.

To prepare reference relaxation data for the guayule plant, four standardized samples with known natural rubber concentrations of 2.5, 5, 7 and 11 weight percent were prepared and analyzed using a 0.5 T benchtop Bruker minispec NMR spectrometer. The influence of natural rubber content in guayule on the $^1H$ NMR signal at low fields was evaluated by acquiring raw time domain NMR signals to determine signal intensity and signal width change for samples with different weight percent of natural rubber. The four standardized guayule samples were prepared using the following procedure.

Standardized Sample Preparation

Guayule shrubs were obtained from a harvest. The shrub material was chopped into pieces having an average diameter of 9.5 mm. A soxhlet extraction apparatus was used to remove about 40 grams of resin and natural rubber from the shrub materials with an acetone/pentane (19/81) azeotrope. Natural rubber was obtained from the extracted shrub material by using acetone/hexane extraction-coagulation method from guayule latex. Resin was further removed from the obtained natural rubber by using an acetone soxhlet extraction. The extracted, resin-free natural rubber from the obtained guayule shrub material was mixed with hexane to prepare four solutions having concentrations of 2.5, 5, 7 and 11 weight percent natural rubber.

Extracted rubber-free guayule shrub materials from above were mixed with four separate guayule rubber solutions at different concentrations in hexane. After mixing, the hexane solvent was evaporated in a fume hood to result in dry material. The resulting material was further dried in a vacuum oven at about 70° C. overnight. Four final guayule shrub samples were prepared for NMR testing. The four samples respectively had a dry weight based natural rubber content of 2.5, 5, 7 and 11 weight percent.

Generation of NMR Signal Intensity Data

FIG. 1 shows the measured time domain signal intensity for each of the four guayule shrub samples. The NMR signal intensity was observed to increase as the weight percent of polyisoprene was increased in a test sample. As such, the standardized guayule sample having a natural rubber content of 11 weight percent resulted in the highest signal intensity of about 35 at zero time whereas the 2.5 weight percent standardized sample had an intensity of about 17.5 at zero time. It is believed that the signal intensity can vary with the mass of the guayule test sample and extractable rubber in the sample and thus making normalization of reference data based on signal intensity alone difficult and susceptible to error.

Figure 2:
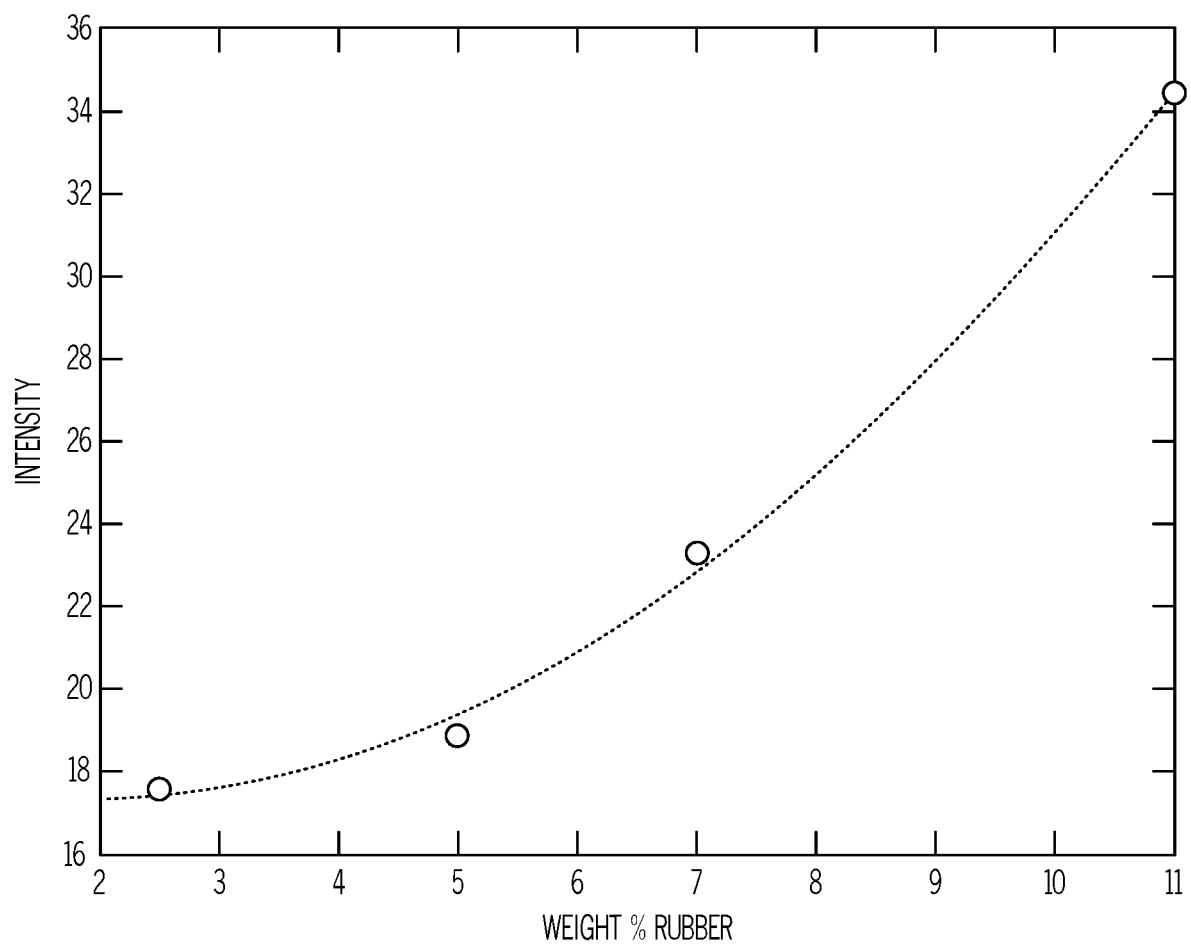
FIG. 2 shows a NMR reference data plot of time domain low-field NMR signal intensity versus weight percent polyisoprene for standardized guayule shrub samples.

FIG. 2 shows the time domain signal intensity data of FIG. 1 plotted against weight percent of polyisoprene. As shown in FIG. 2, the weight percent of polyisoprene versus time domain signal intensity at zero time is not a linear relationship. The non-linear relationship between signal intensity and weight percent of polyisoprene can increase error in predicting the amount of natural rubber in sampled plants as the weight percent of rubber in the plant sample increases.

Figures 3, 4:
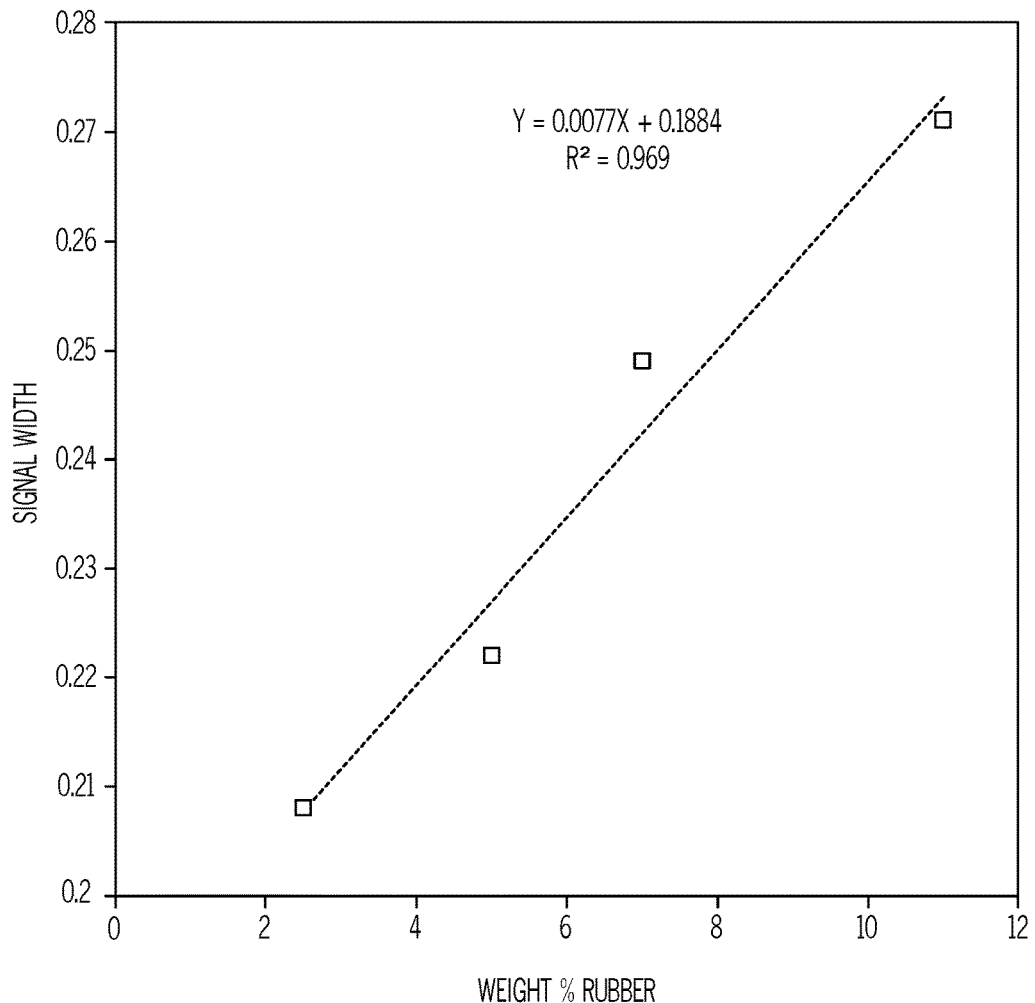
FIG. 3 shows a reference data plot of time domain low-field NMR signal width versus weight percent polyisoprene for standardized guayule shrub samples.
FIG. 4 shows a table of time domain low-field NMR signal width, $T_1$ spin-lattice relaxation rate and $T_2$ spin-spin relaxation rate for four standardized guayule shrub samples having 2.5, 5, 7 and 11 weight percent polyisoprene.

FIG. 3 shows the measured signal width for each of the four guayule shrub samples. The NMR signal width was observed to increase as the weight percent of polyisoprene was increased in each of the four test samples. The signal width was respectively 0.208, 0.222, 0.249 and 0.271 for the samples having 2.5, 5, 7 and 11 weight percent natural rubber. A trend line and a trend line equation were generated for the signal width data to show an approximate linear relationship. It is believed that signal width would similarly suffer from providing varying results as the mass of the guayule test sample changed.

FIG. 4 shows a table of the measured signal width, $T_1$ spin-lattice relaxation rate and the $T_2$ spin-spin relaxation rates over time for each of the four guayule shrub samples. The measured signal widths for each sample are also plotted in FIG. 3 as discussed above. Two sets of $T_2$ spin-spin relaxation rates were taken. The measured $T_2(2)$ relaxation rates were for a slower decaying component, A(2), and the $T_2(1)$ relaxation rates were for a faster decaying component, A(1). It was observed that the $T_2$ relaxation rates for the slower decaying component were in the range of 10.8 to 19.3 ms for the four samples and the $T_2$ relaxation rates for the faster decaying component were in the range of 1.25 to 1.71 ms. It was also observed that the $T_1$ relaxation rates for the faster decaying component were in the range of 27 to 76 ms for the four samples. The $T_2(1)$ relaxation rates for the rapid decaying component, A(1), are significantly similar to $T_2$ relaxation rates measured for the guayule shrub material with a high-field NMR apparatus operating at a magnetic field strength of 11.7 T and a resonance frequency of 500 MHz.

The $T_2(1)$ relaxation rates and the high-field NMR $T_2$ relaxation rates are plotted as standardized reference relaxation data versus weight percent polyisoprene in FIG. 5. The low-field $T_2$ relaxation rates are labeled Minispec and the high-field relaxation rates are labeled 500 MHz. A trend line and corresponding trend line equation for each set of $T_2$ relaxation data was generated using single exponential fitting. FIG. 5 shows a linear relationship between measured $T_2$ spin-spin relaxation rates on a low-field NMR apparatus versus weight percent polyisoprene in a guayule plant. As shown, the $T_2$ spin-spin relaxation rate over time linearly decreases with increasing concentration of natural rubber in a guayule plant. FIG. 5 shows that $T_2$ spin-spin relaxation rates are directly influenced by the amount of natural rubber in a guayule plant and thus standardized reference relaxation data, such as the $T_2$ data in FIG. 5, can be used to quantify the amount of natural rubber in a plant by comparing the reference data to individual plant test data.

The measured $T_1(1)$ relaxation rates of FIG. 4 are plotted as standardized reference relaxation data versus weight percent polyisoprene in FIG. 6. A trend line and corresponding trend line equation for the $T_1$ relaxation data was generated using single exponential fitting. FIG. 6 shows a linear relationship between measured $T_1$ spin-lattice relaxation rates on a low-field NMR apparatus versus weight percent polyisoprene in a guayule plant. As shown, the $T_1$ spin-lattice relaxation rate over time linearly decreases with increasing concentration of natural rubber in a guayule plant. FIG. 6 shows that $T_1$ spin-lattice relaxation rates are directly influenced by the amount of natural rubber in a guayule plant and thus standardized reference relaxation data, such as the $T_1$ data in FIG. 6, can be used to quantify the amount of natural rubber in a plant by comparing the reference data to individual plant test data. Standardized reference relaxation data similar to that plotted in FIGS. 5 and 6 can be used to quantify natural rubber in plants other than guayule as shown.

Example 2

Figure 7:
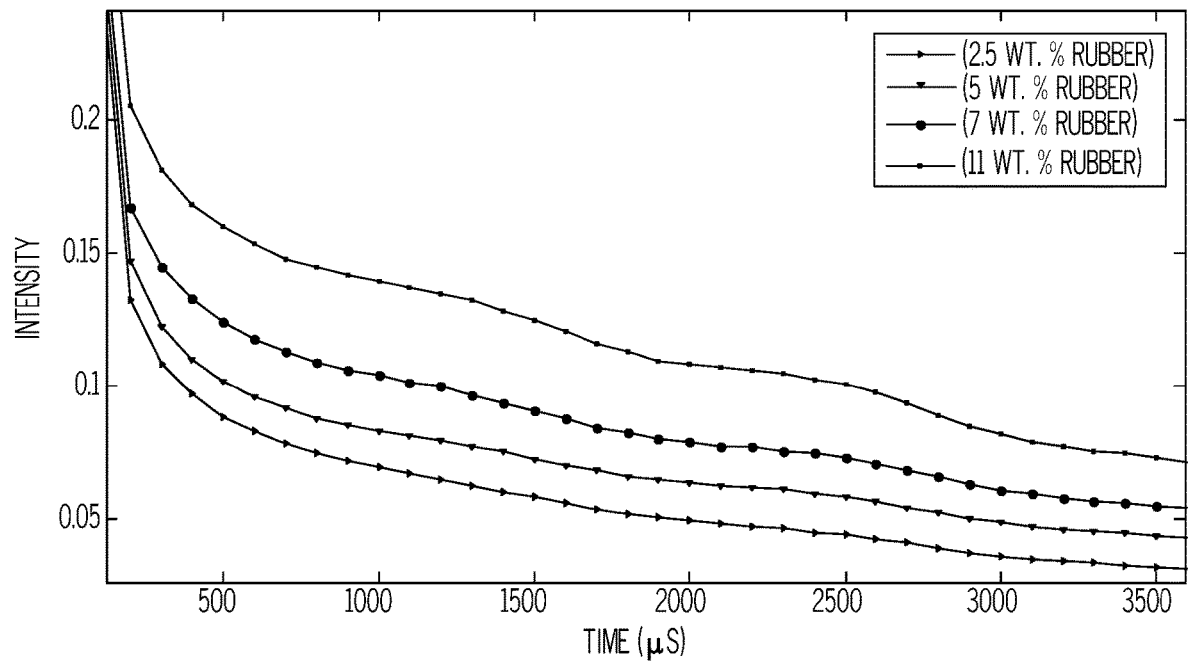
FIG. 7 shows a NMR reference data plot of time domain NMR signal intensity for standardized guayule shrub samples having 2.5, 5, 7 and 11 weight percent polyisoprene.

FIG. 7 shows another example of the measured time domain signal intensity for each of the four guayule shrub samples from Example 1. The NMR signal intensity was observed to increase as the weight percent of polyisoprene was increased in a test sample. As such, the standardized guayule sample having a natural rubber content of 11 weight percent resulted in the highest signal intensity whereas the 2.5 weight percent standardized sample had the lowest intensity.

Figure 9:
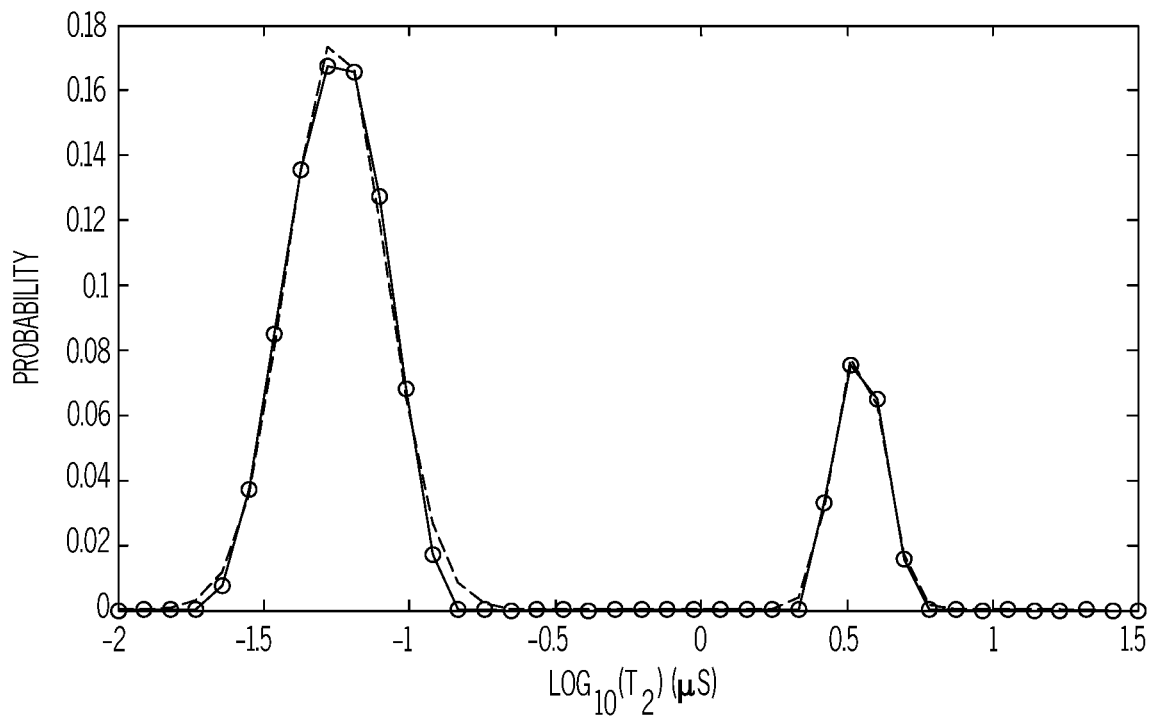
FIG. 9 shows the peaks for the components of the tested samples represented in FIG. 8.

An inverse Laplace transform (ILT) was used to show the $T_2$ distribution from chosen data. FIG. 8 shows the ILT processed $T_2$ relaxation curve of FIG. 7. The first peak at about −1.25 μs ($\log_{10}(T_2)$) in FIG. 8 is for the plant material and the last peak at about a $T_2$ in the range of 0.25 to 0.75 μs ($\log_{10}(T_2)$) is representative of contributions from the rubber and resin. In each of the figures, the samples having the highest rubber content resulted in the highest peaks for the plant material whereas the samples with the highest rubber content resulted in the highest peaks for the contribution of rubber and resin. The intensity ratio is calculated for each data set to determine the intensity ratio. FIG. 9 shows the plant material peak and the rubber and resin peak. The plant material peak contributes 81 percent of the total peak area and the rubber and resin peak contributes 19 percent of the total peak area.

FIG. 10 shows how the ratio of percent area of the rubber and resin component changes as the weight percent of rubber in a sample increases. FIG. 10 represents a reference calibration curve or chart of reference percent area of a rubber/resin peak calculated from standardized rubber and resin spiked samples. A calibration curve can be prepared for any type of rubber-containing plant, for example, the guayule. A trend line shown in FIG. 10 and is characterized by the equation y=85.872x+5.2951, wherein the "y" variable is the weight percent of rubber in a sample and the "x" variable is the percent area under the curve of a rubber/resin component in the sample, which is determined by applying an inverse Laplace transform to the generated $T_2$ spin-spin relaxation rate over time. The measured $T_2$ spin-spin relaxation rate of a guayule plant sample can be processed by ILT to show a peak for the rubber and resin component and the percent area of the peak can be calculated and inserted into the trend line equation to directly calculate or estimate the amount of polyisoprene in the guayule plant being tested.

The use of a calibration curve, for example as shown in FIG. 10, generated from standardized plant samples having known rubber and resin contents provides for an accurate method for quantifying an amount of natural rubber in a plant by use of NMR. A plant sample can be tested by use of an NMR apparatus such as a low-field NMR to obtain NMR relaxation rate, for example the $T_2$ spin-spin relaxation rate, by performing NMR relaxometry on the sample. The relaxation data can be processed as sample intensity or relaxation rate over time, which can be further processed by ILT program or package to generate peaks that represent different components of the plant sample (e.g., plant material, rubber and resin) over time. The percent area under the peak that corresponds to the rubber and resin component can be calculated and compared to a calibration curve of known standardized samples of the same plant type to quantify an amount of natural rubber (e.g., extractable rubber) in the newly sampled plant.

Example 3

Generation of Reference Relaxation Data for Guayule Plant.

To prepare reference relaxation data for the guayule plant, twenty-four standardized samples with known natural rubber and resin concentrations were prepared and analyzed using a 11.7 T, (500 MHz for $^1$H) Varian Innova NMR spectrometer using a Carr-Purcell-Meiboom-Gill (CPMG) sequence. The influence of natural rubber and resin content in guayule on the $^1$H NMR signal at high fields was evaluated by acquiring raw time domain NMR signals to determine signal intensity and signal width change for samples with different weight percent of natural rubber and resin.

The natural rubber and resin concentrations of the twenty-four samples are shown in Table 1 below. One unit of rubber equals 0.023 g and one unit of resin equals 0.019 g.

TABLE 1

| Sample | Units Rubber | Units Resin | Wt % Rubber | Wt % Resin |
|---|---|---|---|---|
| 1-00 | 0 | 0 | 0 | 0 |
| 1-01 | 0 | 1 | 0 | 1.86 |
| 1-02 | 0 | 2 | 0 | 3.66 |
| 1-03 | 0 | 3 | 0 | 5.39 |
| 1-04 | 0 | 4 | 0 | 7.06 |
| 1-05 | 0 | 5 | 0 | 8.68 |
| 1-10 | 1 | 0 | 2.25 | 0 |
| 1-11 | 1 | 1 | 2.21 | 1.82 |
| 1-12 | 1 | 2 | 2.17 | 3.58 |
| 1-13 | 1 | 3 | 2.13 | 5.28 |
| 1-14 | 1 | 4 | 2.09 | 6.92 |
| 1-15 | 1 | 5 | 2.06 | 8.50 |
| 1-30 | 3 | 0 | 6.45 | 0 |
| 1-31 | 3 | 1 | 6.34 | 1.75 |
| 1-32 | 3 | 2 | 6.23 | 3.43 |
| 1-33 | 3 | 3 | 6.13 | 5.06 |
| 1-34 | 3 | 4 | 6.03 | 6.64 |
| 1-35 | 3 | 5 | 5.93 | 8.16 |
| 1-50 | 5 | 0 | 8.7 | 0 |
| 1-51 | 5 | 1 | 8.5 | 2.1 |
| 1-52 | 5 | 2 | 8.3 | 4 |
| 1-53 | 5 | 3 | 8.2 | 5.9 |
| 1-54 | 5 | 4 | 8.0 | 7.8 |
| 1-55 | 5 | 5 | 7.9 | 9.5 |

Figure 11:
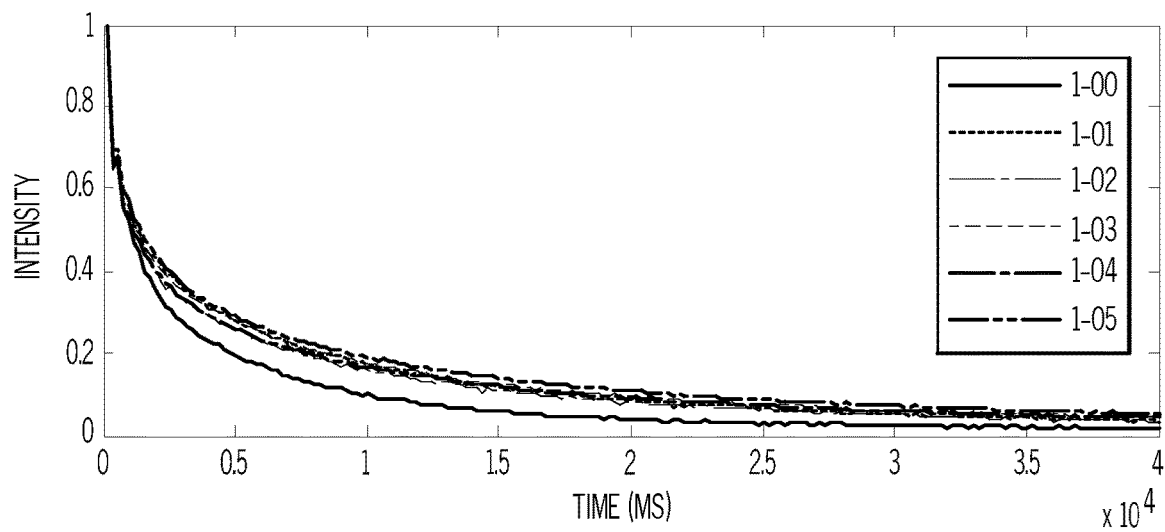
FIG. 11 shows a NMR reference data plot of time domain NMR signal intensity for standardized samples having known amounts of rubber and resin.
Figure 12:
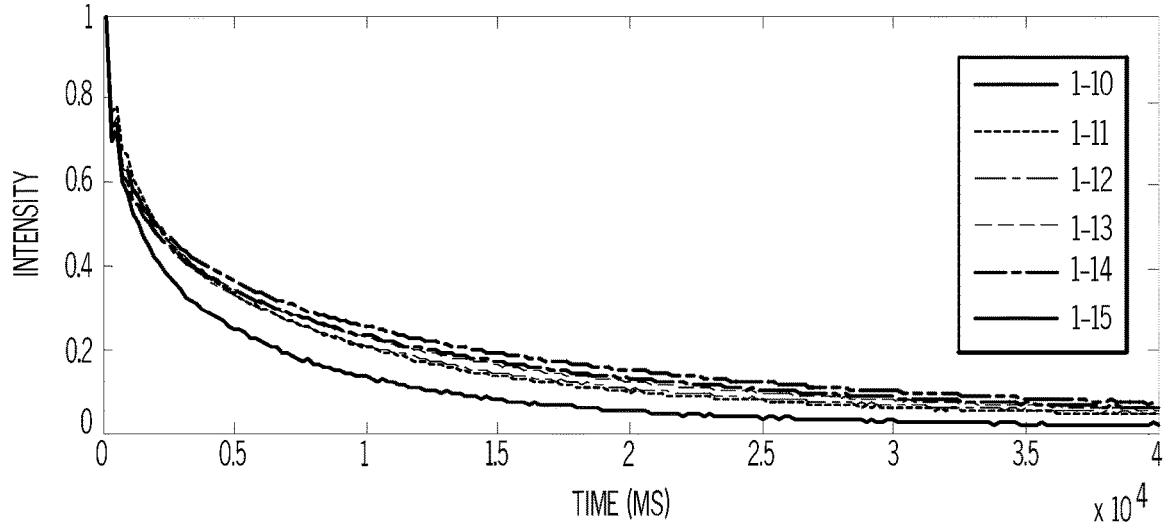
FIG. 12 shows a NMR reference data plot of time domain NMR signal intensity for standardized samples having known amounts of rubber and resin.
Figure 13:
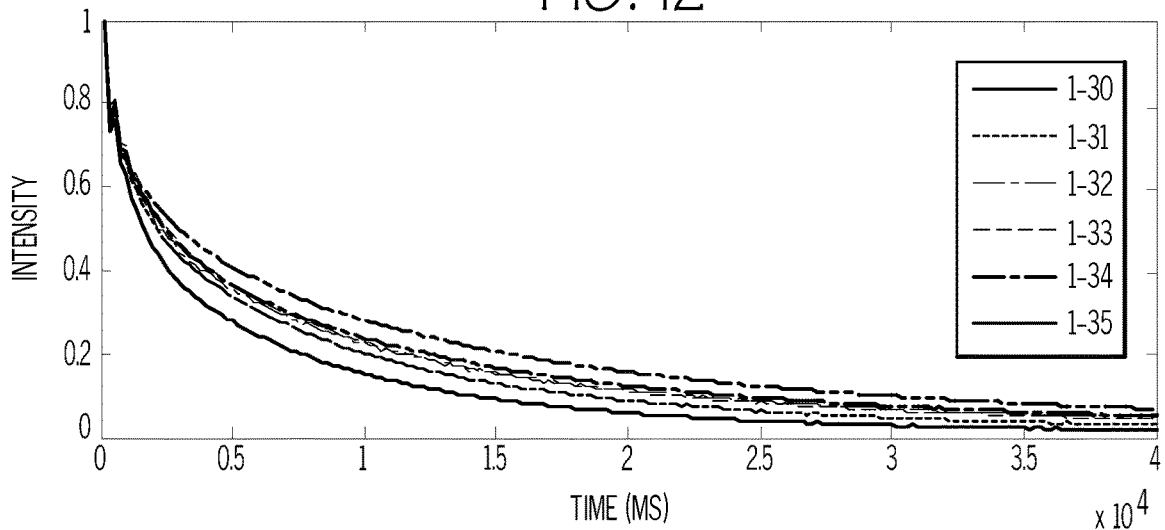
FIG. 13 shows a NMR reference data plot of time domain NMR signal intensity for standardized samples having known amounts of rubber and resin.

Generation of NMR Signal Intensity Data $T_2$ relaxation curves were generated using $^1$H CPMG sequence. FIG. 11 shows the measured time domain signal intensity for each of the first six samples (i.e. 1-00, 1-01, 1-02, 1-03, 1-04 and 1-05). FIG. 12 shows the measured time domain signal intensity for each of the second six samples (i.e. 1-10, 1-11, 1-12, 1-13, 1-14 and 1-15). FIG. 13 shows the measured time domain signal intensity for each of the third six samples (i.e. 1-30, 1-31, 1-32, 1-33, 1-34 and 1-35). In each of the figures, the samples having the highest natural rubber content resulted in the highest signal intensity whereas the samples with the lowest rubber content had the lowest intensity at zero time. It is believed that the signal intensity can vary with the mass of the guayule test sample and extractable rubber in the sample and thus making normalization of reference data based on signal intensity alone difficult and susceptible to error.

An inverse Laplace transform (ILT) was used to show the $T_2$ distribution from chosen data. FIG. 14 shows the ILT processed $T_2$ relaxation curve of FIG. 11 for samples 1-00, 1-01, 1-02, 1-03, 1-04 and 1-05. FIG. 15 shows the ILT processed $T_2$ relaxation curve of FIG. 12 for samples 1-10, 1-11, 1-12, 1-13, 1-14 and 1-15. FIG. 16 shows the ILT processed $T_2$ relaxation curve of FIG. 13 for samples 1-30, 1-31, 1-32, 1-33, 1-34 and 1-35.

The first peak at about 5 ms in FIGS. 14, 15 and 16 is for the plant material and the second peak at about a $T_2$ in the range of 20 to 40 ms is representative of contributions from the rubber and resin. In each of the figures, the samples having the lowest rubber content resulted in the highest peaks for the plant material whereas the samples with the highest rubber content resulted in the highest peaks for the contribution of rubber and resin.

The intensity ratio can be calculated for each data set of relaxation rate and ILT processed peaks to determine intensity ratio. For example, a graph similar to that shown in FIG. 9 can be generated to show the ratio of the plant material peak as compared to the rubber and resin peak. The percent area of the plant material peak and the rubber and resin peak can be calculated, which can be used to determine the ratio of percent areas for the total peak area.

From the intensity ratio of peak areas for the different plant components (e.g., plant material, rubber and resin), a reference calibration curve can be created to show how the ratio of percent area of the rubber and resin component changes as the weight percent of rubber in a sample increases. The use of standardized plant samples with know spiked rubber and resin contents can validate the generated calibration curve so it can be used as an accurate method for quantifying an amount of natural rubber in a plant by use of NMR. For example, a trend line can be determined for the plotted data to relate the weight percent of rubber in a sample to the the percent area under the curve of a rubber/resin component in the sample, which is determined by applying an inverse Laplace transform to the generated $T_2$ spin-spin relaxation rate over time.

The accuracy of the methods for quantifying an amount of natural rubber in a plant by using NMR and applying an ILT to the NMR relaxation rate data and further generating a calibration curve to relate the ratio of peak areas to weight percent rubber in a sample are minimally affected by the presence of resin in a plant sample. Thus, the methods can be carried out without the need for extra steps of removing or extracting resin from a plant sample as opposed to less efficient methods that result in less accurate quantification of rubber due to the presence of resin.

FIG. 17 shows that the presence of resin in a plant sample does not significantly alter or affect the accuracy of methods of the present disclosure. As shown, the ratio of the rubber and resin component to the plant material component in the ILT processed NMR relaxation rate data is plotted on the y axis and the weight percent of rubber in each standardized sample is plotted on the x axis. 0 parts resin to 5 parts resin does not exhibit a pattern of affecting the processed ratio. For example, at the highest rubber content for the standardized samples (around 8 wt %), the 0 parts resin and the 5 parts resin samples exhibited about a 5% difference in ratio of the rubber and resin component to the plant material component in the ILT processed NMR relaxation rate data. On average, the methods using ILT processed NMR relaxation rate data to calculate a calibration curve can quantify the amount of natural rubber in a plant sample with an accuracy of within 10 percent, preferably 8 percent and more preferably 6 percent, or 5, 4 or 3 percent of the actual amount of rubber in a tested plant.

FIG. 18 further evidences that the presence of resin in a plant sample does not significantly alter or affect the accuracy of method of the present disclosure. As shown, the intensity of the rubber and resin component of the ILT processed NMR relaxation rate data of Table 1 is plotted against the weight percent of rubber in the standardized samples. 0 parts resin to 3 parts resin does not exhibit a pattern of affecting the intensity of the rubber and resin component of the ILT processed NMR relaxation rate data. For example, at the highest rubber content for the standardized samples (around 8-9 wt %), the 1 part resin and the 3 part resin samples, as each compared to the 0 part resin sample, respectively exhibited about a 15% and about a 11% difference.

All references, including but not limited to patents, patent applications, and non-patent literature are hereby incorporated by reference herein in their entirety.

While various aspects and embodiments have been disclosed herein, other aspects and embodiments will be apparent to those skilled in the art. The various aspects and embodiments disclosed herein are for purposes of illustration and are not intended to be limiting.

What is claimed is:

1. A method for quantifying an amount of natural rubber in a rubber-containing plant by use of NMR, comprising the steps of:
   a. introducing a portion of the plant comprising natural rubber and resin into a sample receiving space of a NMR apparatus, wherein obtaining the portion of the plant is non-destructive to the plant;
   b. obtaining a NMR relaxation rate by performing NMR relaxometry on the portion of the plant using the NMR apparatus, the NMR relaxation rate being a $T_2$ spin-spin relaxation rate of the portion of the plant over time;
   c. processing the $T_2$ spin-spin relaxation rate using inverse Laplace transformation to generate a chart having one peak representing the natural rubber and resin content of the portion of the plant;
   d. quantifying the amount of natural rubber in the plant by comparing the NMR relaxation rate obtained from the portion of the plant in step (c) to a reference calibration curve generated from a NMR relaxation rate obtained from testing the same type of plant as the portion of the plant from step (a).

2. The method of claim 1, the plant being guayule and the amount of quantified natural rubber being the amount of extractable natural rubber contained the guayule plant being tested.

3. The method of claim 1, the method being non-destructive to the plant wherein the portion of the plant used in the sample receiving space of the NMR apparatus to quantify an amount of natural rubber in the plant is less than 5 weight percent of the plant.

4. The method of claim 1, the NMR apparatus operating at a magnetic field strength of 2 T or less for obtaining the NMR relaxation rate for the portion of the plant.

5. The method of claim 1, the method being performed on the portion of the plant in less than 10 minutes and the NMR apparatus being a low-field NMR apparatus.

6. The method of claim 1, the reference relaxation curve being a reference relaxation plot of the $T_2$ spin-spin relaxation rate versus weight percent polyisoprene for the same type of plant as the portion of the plant from step (a).

7. The method of claim 1, the method further comprising quantifying an amount of resin in the plant by comparing the NMR relaxation rate obtained from the portion of the plant in step (c) to the reference calibration curve, the reference calibration curve being a plot of the $T_2$ spin-spin relaxation rate versus weight percent resin for the same type of plant as the portion of the plant from step (a).

8. The method of claim 1, the calibration curve being a plot of the percent area of the peak representing the natural rubber and resin content of the portion of the plant to the total peak area of the chart versus weight percent rubber to quantify the amount of natural rubber in the plant.

9. The method of claim 1, the calibration curve being a plot of the ratio of the area of the peak representing the natural rubber and resin content of the portion of the plant to the total peak area versus weight percent rubber to quantify the amount of natural rubber in the plant.

10. The method of claim 1, the calibration curve being a plot of the intensity of the peak representing the natural rubber and resin content of the portion of the plant versus weight percent rubber to quantify the amount of natural rubber in the plant.

11. The method of claim 1, the portion of the plant having at least 1 weight percent resin based on the total weight of the portion of the plant introduced into the receiving space of the NMR apparatus.

12. A non-destructive method for quantifying an amount of natural rubber in a guayule plant by use of low-field NMR, comprising the steps of:
   a. introducing a portion of the guayule plant comprising natural rubber and resin into a sample receiving space of a low-field NMR apparatus, the low-field NMR apparatus operating at a magnetic field strength of 2 T or less and at 90 MHz or less for obtaining a NMR relaxation rate for the portion of the guayule plant;
   b. obtaining a $T_2$ spin-spin relaxation rate of the portion of the guayule plant over time and processing the $T_2$ spin-spin relaxation rate obtained for the portion of the guayule plant using inverse Laplace transformation to generate a chart having one peak representing the natural rubber and resin content of the portion of the plant;
   c. quantifying the amount of natural rubber in the guayule plant by comparing the $T_2$ spin-spin relaxation rate of the portion of the guayule plant to a reference calibration curve generated from a NMR relaxation rate obtained from testing the same type of plant as the portion of the plant from step (a).

13. The method of claim 12, the calibration curve being a plot of the percent area of the peak representing the natural rubber and resin content of the portion of the guayule plant to the total peak area of the chart versus weight percent polyisoprene to quantify the amount of natural rubber in the guayule plant.

* * * * *